(12) United States Patent
Mason et al.

(10) Patent No.: US 10,265,141 B2
(45) Date of Patent: Apr. 23, 2019

(54) DENTAL APPLIANCE WITH SIMULATED TEETH AND METHOD FOR MAKING

(71) Applicant: Align Technology, Inc., San Jose, CA (US)

(72) Inventors: David Mason, Morgan Hill, CA (US); Eric Kuo, Foster City, CA (US)

(73) Assignee: Align Technology, Inc., San Jose, CA (US)

(*) Notice: Subject to any disclaimer, the term of this patent is extended or adjusted under 35 U.S.C. 154(b) by 273 days.

(21) Appl. No.: 14/533,917

(22) Filed: Nov. 5, 2014

(65) Prior Publication Data

US 2015/0128421 A1  May 14, 2015

Related U.S. Application Data

(62) Division of application No. 12/277,153, filed on Nov. 24, 2008, now Pat. No. 8,936,463.

(51) Int. Cl.
| | |
|---|---|
| *A61C 7/08* | (2006.01) |
| *A61C 7/00* | (2006.01) |
| A61C 13/107 | (2006.01) |
| A61C 5/20 | (2017.01) |

(52) U.S. Cl.
CPC .............. *A61C 7/08* (2013.01); *A61C 7/002* (2013.01); *A61C 5/20* (2017.02); *A61C 13/0001* (2013.01); *Y10T 29/49568* (2015.01)

(58) Field of Classification Search
CPC .. A61C 7/00; A61C 7/08; A61C 7/002; A61C 13/00; A61C 13/0001; Y10T 29/49568
USPC ................ 433/6, 24; 128/861–862
See application file for complete search history.

(56) References Cited

U.S. PATENT DOCUMENTS

| | | | |
|---|---|---|---|
| 2,467,432 A | 4/1949 | Kesling | |
| 3,407,500 A | 10/1968 | Kesling | |
| 3,600,808 A | 8/1971 | Reeve | |
| 3,660,900 A | 5/1972 | Andrews | |
| 3,683,502 A | 8/1972 | Wallshein. | |
| 3,738,005 A | 6/1973 | Cohen | |

(Continued)

FOREIGN PATENT DOCUMENTS

| | | |
|---|---|---|
| AU | 3031677 A | 5/1979 |
| AU | 517102 B2 | 7/1981 |

(Continued)

OTHER PUBLICATIONS

AADR. American Association for Dental Research, Summary of Activities, Mar. 20-23, 1980, Los ngeles, CA, p. 195.

(Continued)

*Primary Examiner* — Edward Moran

(74) *Attorney, Agent, or Firm* — Wilson Sonsini Goodrich & Rosati

(57) ABSTRACT

The present invention relates to orthodontic positioning appliances that represent teeth in desired positions and related systems and methods. An appliance can include teeth receiving cavities shaped to receive and apply a resilient positioning force to a patient's teeth. An appliance can include an outer component having a surface representing teeth in desired positions. An outer component can be integral with an appliance. An outer component can be separate and configured to couple with an appliance main body.

12 Claims, 10 Drawing Sheets

(56) References Cited

U.S. PATENT DOCUMENTS

| | | |
|---|---|---|
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,764,115 A | 8/1988 | Willits et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adeli |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,431,562 A | 11/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A * | 11/1999 | Chishti .............. A61C 7/00 433/24 |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordon et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier |
| 6,398,548 B1 | 6/2002 | Muhammad et al. |
| 6,402,707 B1 | 6/2002 | Ernst |
| 6,450,807 B1 | 9/2002 | Chishti et al. |
| 6,482,298 B1 | 11/2002 | Bhatnagar |
| 6,524,101 B1 | 2/2003 | Phan et al. |
| 6,554,611 B2 | 4/2003 | Chishti et al. |
| 6,572,372 B1 | 6/2003 | Phan et al. |
| 6,629,840 B2 | 10/2003 | Chishti et al. |
| 6,705,863 B2 | 3/2004 | Phan et al. |
| 6,722,880 B2 | 4/2004 | Chishti et al. |
| 6,830,450 B2 * | 12/2004 | Knopp .............. A61C 7/08 433/18 |
| 7,320,592 B2 | 1/2008 | Chishti et al. |
| 7,357,637 B2 | 4/2008 | Leichtung |
| 7,481,121 B1 | 1/2009 | Cao |
| 2002/0006597 A1 | 1/2002 | Andreiko et al. |

(56) References Cited

U.S. PATENT DOCUMENTS

| | | | |
|---|---|---|---|
| 2002/0187451 A1* | 12/2002 | Phan | A61C 7/00 433/6 |
| 2002/0192617 A1* | 12/2002 | Phan | A61C 7/00 433/6 |
| 2003/0003416 A1* | 1/2003 | Chishti | A61C 7/00 433/24 |
| 2003/0008259 A1* | 1/2003 | Kuo | A61C 7/00 433/6 |
| 2003/0009252 A1 | 1/2003 | Pavlovskaia et al. | |
| 2003/0136416 A1 | 7/2003 | White | |
| 2003/0139834 A1 | 7/2003 | Nikolskiy et al. | |
| 2003/0224311 A1 | 12/2003 | Cronauer | |
| 2004/0009449 A1 | 1/2004 | Mah et al. | |
| 2004/0128010 A1 | 7/2004 | Pavlovskaia et al. | |
| 2005/0055118 A1 | 3/2005 | Nikolskiy et al. | |
| 2006/0008760 A1 | 1/2006 | Phan et al. | |
| 2006/0093983 A1* | 5/2006 | Schultz | A61C 7/08 433/6 |
| 2006/0216670 A1 | 9/2006 | Leichtung | |
| 2007/0231765 A1 | 10/2007 | Phan et al. | |
| 2008/0003541 A1 | 1/2008 | Leslie-Martin | |
| 2008/0120878 A1* | 5/2008 | Smith | G09F 21/02 40/586 |
| 2010/0104998 A1 | 4/2010 | Farrell et al. | |
| 2010/0129762 A1 | 5/2010 | Mason et al. | |

FOREIGN PATENT DOCUMENTS

| | | |
|---|---|---|
| AU | 5598894 A | 6/1994 |
| CA | 1121955 | 4/1982 |
| DE | 2749802 | 5/1978 |
| DE | 69327661 T | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 8/1995 |
| EP | 0731673 B1 | 9/1996 |
| EP | 0774933 B1 | 5/1997 |
| ES | 463897 | 1/1980 |
| FR | 2369828 A1 | 6/1978 |
| FR | 2652256 A1 | 3/1991 |
| GB | 15500777 | 8/1979 |
| JP | 53-058191 | 5/1978 |
| JP | 04-028359 | 1/1992 |
| JP | 08-508174 | 9/1996 |
| WO | WO 90/08512 A1 | 8/1990 |
| WO | WO 91/04713 A1 | 4/1991 |
| WO | WO 94/10935 A1 | 5/1994 |
| WO | WO 98/32394 A1 | 7/1998 |
| WO | WO 98/44865 A1 | 10/1998 |
| WO | WO 98/58596 A1 | 12/1998 |

OTHER PUBLICATIONS

Alcaniz, et aL, "An Advanced System for the Simulation and Planning of Orthodontic Treatments," Karl HF Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler et al., "Analysis of 3-D Data for Comparative 3-D Serial Growth Pattern Studies of Oral-Facial Structures," AADR Abstracts, Program and Abstracts of Papers, 57th General Session, IADR HP Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging q Applications for Automated Industrial Inspection and Assembly, vol. 182, p. 187-191 (1979).

Altschuler, "3D Mapping of Maxillo-Facial Prosthesis," AADR Abstract #607, 2 pages total, (1980).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of III., Aug. 26-30, 1975, pp. 142-166.

Baumrind, "Integrated Three-Dimensional Craniofacial Mapping: Background, Principles, and Perspectives," Semin. in Orthod., 7(4):223-232 (Dec. 2001).

Begole et al., "A Computer System for the Analysis of Dental Casts," The Angle Orthod., 51(3):253-259 (Jul. 1981).

Bernard et al.,"Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.

Bhatia et al., "A Computer-Aided Design for Orthognathic Surgery," Br. J. Oral Maxillofac. Surg., 22:237-253 (1984).

Biggerstaff et al., "Computerized Analysis of Occlusion in the Postcanine Dentition," Am. J. Orthod., 61(3): 245-254 (Mar. 1972).

Biggerstaff, "Computerized Diagnostic Setups and Simulations," Angle Orthod., 40(1):28-36 (Jan. 1970).

Biostar Opeation & Training Manual. Great Lakes Orthodontics, Ltd. 199 Fire Tower Drive, Tonawanda, New York. 14150-5890, 20 pages total (1990).

Blu, et al., "Linear interpolation revitalized", IEEE Trans. Image Proc., 13(5):710-719 (May 2004.

Bourke, "Coordinate System Transformation," (Jun. 1996), p. 1, retrieved from the Internet Nov. 5, 2004. URL <http://astronomy.swin.edu.au/-pbourke/prolection/coords>.

Boyd et al., "Three Dimensional Diagnosis and Orthodontic Treatment of Complex Malocclusions With the Invisalipn Appliance," Semin. Orthod., 7(4):274-293 (Dec. 2001).

Brandestini et al., "Computer Machined Ceramic Inlays: In Vitro Marginal Adaptation," J. Dent. Res. Special Issue, Abstract 305, vol. 64, p. 208 (1985).

Brook et al., "An Image Analysis System for the Determination of Tooth Dimensions from Study Casts: IK Comparison with Manual Measurements of Mesio-distal Diameter," J. Dent. Res., 65(3):428-431 (Mar. 1986.

Burstone (interview), "Dr. Charles J. Burstone on the Uses of the Computer in Orthodontic Practice (Part 1)," J. Clin. Orthod., 13(7):442-453 (Jul. 1979).

Burstone (interview), "Dr. Charles J. Burstone on the Uses of the Computer in Orthodontic Practice (Part 2)," J. Clin. Orthod., 13(8):539-551 (Aug. 1979.

Burstone et al., Precision Adjustment of the Transpalatal Lingual Arch: Computer Arch Form IN Predetermination, Am, Journal of Orthodontics, vol. 79, No. 2 (Feb. 1981), pp. 115-133.

Cardinal Industrial Finishes, Powder Coatings information posted at <http://www.cardinalpaint.com> on Aug. 25, 2000, 2 pages.

Carnaghan, "An Alternative to Holograms for the Portrayal of Human Teeth," 4th Int'l. Conf. on Holographic Systems, Components and Applications, Sep. 15, 1993, pp. 228-231.

(56) References Cited

OTHER PUBLICATIONS

Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1: CAD/CAM: The Computer Moves Chairside," "Part 2: F. Duret—A Man With a Vision," "Part 3: The Computer Gives New Vision—Literally," "Part 4: Bytes 'N Bites" The Computer Moves From the Front Desk to the Operatory, Canadian Dental Journal, vol. 54(9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et al., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCD Titan System' for Production of Crowns/Bridges," DSC Production AG, pp. 1-7 (Jan. 1992.
Definition for gingiva. Dictionary.com p. 1-3. Retrieved from the internet Nov. 5, 2004 <http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
Dentrac Corporation, Dentrac document, pp. 4-13 (1992).
Dent-X posted on Sep. 24, 1998 at <http://www.dent-x.com/DentSim.htm>, 6 pages.
Doyle, "Digital Dentistry," Computer Graphics World, pp. 50-52, 54 (Oct. 2000.
DuraClearTM product information, Allesee Orthodontic Appliances-Pro Lab, 1 page (1997).
Duret et al, "CAD-CAM in Dentistry," J. Am. Dent. Assoc. 117:715-720 (Nov. 1988.
Duret et al., "CAD/CAM Imaging in Dentistry," Curr. Opin. Dent., 1:150-154 (1991.
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979.
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987.
Friede et al., "Accuracy of Cephalometric Prediction in Orthognathic Surgery," Abstract of Papers, J. Dent. Res., 70:754-760 (1987.
Futterling et a/., "Automated Finite Element Modeling of a Human Mandible with Dental Implants," JS WSCG '98—Conference Program, retrieved from the Internet: <http://wscg.zcu.cz/wscg98/papers98/Strasser 98.pdf>, 8 pages.

Gao et al., "3-D element Generation for Multi-Connected Complex Dental and Mandibular Structure," Proc. Intl Workshop on Medical Imaging and Augmented Reality, pp. 267-271 (Jun. 12, 2001.
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management,"J. Clin. Orthod., 16(6):390-407 (Jun. 1982.
Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990.
Guess et al., "Computer Treatment Estimates in Orthodontics and Orthognathic Surgery," JCO, pp. 262-28 (Apr. 1989.
Heaven et a/., "Computer-Based Image Analysis of Artificial Root Surface Caries," Abstracts of Papers, J. Dent. Res., 70:528 (Apr. 17-21, 1991.
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressp tonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total.
Hoffmann, et al., "Role of Cephalometry for Planning of Jaw Orthopedics and Jaw Surgery Procedures," 0 (Article Summary in English, article in German), Informatbnen, pp. 375-396 (Mar. 1991.
Hojjatie et al., "Three-Dimensional Finite Element Analysis of Glass-Ceramic Dental Crowns," J. Biomech., 23(11):1157-1166 (1990.
Huckins, "CAD-CAM Generated Mandibular Model Prototype from MRI Data," AAOMS, p. 96 (1999.
Important Tip About Wearing the Red White & Blue Active Clear Retainer System, Allesee Orthodontic Appliances—Pro Lab, 1 page 1998).
Inside the ADA, JADA, 118:286-294 (Mar. 1989).
JCO Interviews, Craig Andreiko , DDS, MS on the Elan and Orthos Systems, JCO, pp. 459-468 (Aug. 1994.
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988.
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling et al., The Philosophy of the Tooth Positioning Appliance, American Journal of Orthodontics and Oral surgery. 1945; 31:297-304.
Kesling, Coordinating the Predetermined Pattern and Tooth Positioner with Conventional Treatment, KN Am. J. Orthod. Oral Surg. (1946) 32:285-293.
KI Kamada et.al., Case Reports on Tooth Positioners Using LTV Vinyl Silicone Rubber, J. Nihon University School of Dentistry (1984) 26(1): 11-29.
Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984).
KM Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.

(56) References Cited

OTHER PUBLICATIONS

Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991).
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989).
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginale Adaptation von adhasuven Porzel-laninlays in vitro," Separatdruck aus: Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, Oct. 22-23, 1990.
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. Of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.
Ponitz, "Invisible Retainers," Am. J. Orthod., 59(3):266-272 (Mar. 1971).
PROCERA Research Projects, "PROCERA Research Projects 1993—Abstract Collection," pp. 3-7, 28 (1993.
Proffit et al., Contemporary Orthodontics, (Second Ed.), Chapter 15, Mosby Inc., pp. 470-533 (Oct. 1993.
Raintree Essix & ARS Materials, Inc., Raintree Essix, Technical Magazine Table of contents and q Essix Appliances, <httpz;//www.essix.com/magazine/defaulthtml> Aug. 13, 1997.
Redmond et al., "Clinical Implications of Digital Orthodontics," Am. J. Orthod. Dentofacial Orthop., 117(2):240-242 (2000.
Rekow et a/., "CAD/CAM for Dental Restorations—Some of the Curious Challenges," IEEE Trans. Biomed. Eng., 38(4):314-318 (Apr. 1991.
Rekow et al., "Comparison of Three Data Acquisition Techniques for 3-D Tooth Surface Mapping," LM Annual International Conference of the IEEE Engineering in Medicine and Biology Society, 13(1):344-345 1991.
Rekow, "A Review of the Developments in Dental CAD/CAM Systems," (contains references to LN Japanese efforts and content of the papers of particular interest to the clinician are indicated with a one line summary of their content in the bibliography), Curr. Opin. Dent., 2:25-33 (Jun. 1992.
Rekow, "CAD/CAM in Dentistry: A Historical Perspective and View of the Future," J. Can. Dent. Assoc., 58(4):283, 287-288 (Apr. 1992.
Rekow, "Computer-Aided Design and Manufacturing in Dentistry: A Review of the State of the Art," J. Prosthet. Dent., 58(4):512-516 (Oct. 1987.
Rekow, "Dental CAD-CAM Systems: What is the State of the Art?", J. Amer. Dent. Assoc., 122:43-48 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Sur9., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992.
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee HI Orthodontic Appliances—Pro Lab product information for doctors. http://ormco.com/aoa/appliancesservices/RWB/doctorhtml>, 5 pages (May 19, 2003).
The Choice is Clear: Red, White & Blue . . . The Simple, Affordable, No-Braces Treatment, Allesee HJ Orthodontic Appliances—Pro Lab product information for patients, <http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances—Pro Lab product information, 6 pages (2003).
The Red, White & Blue Way to Improve Your Smile! Allesee Orthodontic Appliances—Pro Lab product information for patients, 2 pages 1992.
Truax L., "Truax Clasp-Less(TM) Appliance System," Funct. Orthod., 9(5):22-4, Sep. 26-Oct. 8, 1992.
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden et al., "Three-Dimensional Analysis of Dental Casts by Means of the Optocom," J. Dent. Res., p. 1100 (Jul.-Aug. 1972).
Van Der Linden, "A New Method to Determine Tooth Positions and Dental Arch Dimensions," J. Dent. Res., 51(4):1104 (Jul.-Aug. 1972).
Van Der Zel, "Ceramic-Fused-to-Metal Restorations with a New CAD/CAM System," Quintessence Int., 24(11):769-778 (1993.

(56) References Cited

OTHER PUBLICATIONS

Varady et al., "Reverse Engineering of Geometric Models—An Introduction," Computer-Aided Design, 29(4):255-268,1997.

Verstreken et al., "An Image-Guided Planning System for Endosseous Oral Implants," IEEE Trans. Med. Imaging, 17(5):842-852 (Oct. 1998).

Warunek et al., Physical and Mechanical Properties of Elastomers in Orthodonic Positioners, Am J. Orthod. Dentofac. Orthop, vol. 95, No. 5, (May 1989) pp. 399-400.

Warunek et.al., Clinical Use of Silicone Elastomer Applicances, JCO (1989) XXIII(10):694-700.

Wells, Application of the Positioner Appliance in Orthodontic Treatment, Am. J. Orthodont. (1970) 58:351-366.

Williams, "Dentistry and CAD/CAM: Another French Revolution," J. Dent. Practice Admin., pp. 2-5 (Jan./Mar. 1987).

Williams, "The Switzerland and Minnesota Developments in CAD/CAM," J. Dent. Practice Admin., pp. 50-55 (Apr./Jun. 1987).

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.

WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.

Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001.

Yamamoto et al., "Optical Measurement of Dental Cast Profile and Application to Analysis of Three-Dimensional Tooth Movement in Orthodontics," Front. Med. Biol. Eng., 1(2):119-130 (1988).

Yamamoto et al., "Three-Dimensional Measurement of Dental Cast Profiles and Its Applications to Orthodontics," Conf. Proc. IEEE Eng. Med. Biol. Soc., 12(5):2051-2053 (1990).

Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.

Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980.

Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).

Yoshii, "Research on a New Orthodontic Appliance: The Dynamic Positioner (D.P.); Ill.—The General Concept of the D.P. Method and Its Therapeutic Effect, Part 2. Skeletal Reversed Occlusion Case Reports," Nippon Dental Review, 458:112-129 (Dec. 1980.

Yoshii, "Research on a New Orthodontic Appliance: The Dynamic Positioner (D.P.); Ill. The General Concept of the D.P. Method and Its Therapeutic Effect, Part 1, Dental and Functional Reversed Occlusion Case Reports," Nippon Dental Review, 457:146-164 (Nov. 1980).

You May Be a Candidate for This Invisible No-Braces Treatment, Allesee Orthodontic Appliances—Pro Lab product information for patients, 2 pages (2002).

\* cited by examiner

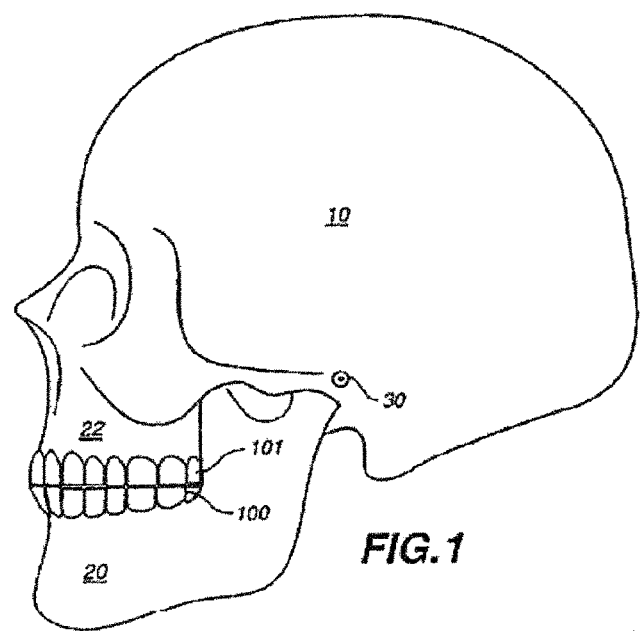
FIG.1
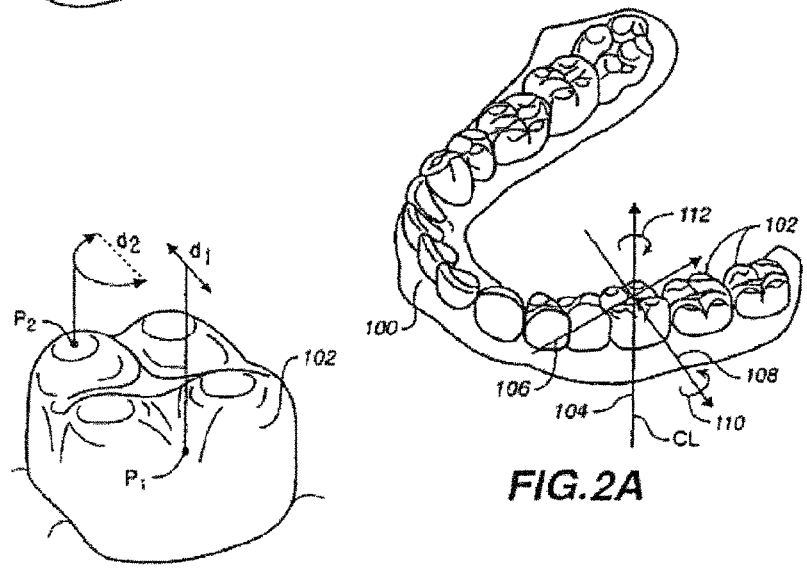
FIG.2A
FIG.2B

DENTAL APPLIANCE WITH SIMULATED TEETH AND METHOD FOR MAKING

CROSS-REFERENCE TO RELATED APPLICATIONS

This application is a divisional of U.S. patent application Ser. No. 12/277,153, filed Nov. 24, 2008, now U.S. Pat. No. 8,936,463, issued Jan. 20, 2015, the full disclosure of which is incorporated herein by reference.

BACKGROUND OF THE INVENTION

The present invention relates generally to the field of orthodontics, and more particularly removable tooth positioning appliances with the appearance of a desired tooth arrangement as well as related methods, including methods of use and fabrication.

An objective of orthodontics is to move a patient's teeth to positions where function and/or aesthetics are improved. Traditionally, orthodontists applied metal brackets to the patient's teeth, and coupled them by a wire and elastics to exert diminishing force on the teeth in a general direction. This force gradually urges the teeth toward a desired stage of treatment. With a series of clinical visits and reactive adjustments to the wire and elastics, the orthodontist can move the teeth through various treatment stages until a final functional and desirable tooth arrangement is obtained.

More recently, alternatives to conventional orthodontic treatment with traditional affixed appliances (e.g., braces) have become available. For example, systems including a series of preformed appliances/aligners have become commercially available from Align Technology, Inc., Santa Clara, Calif., under the trade name Invisalign® System. The Invisalign® System is described in numerous patents and patent applications assigned to Align Technology, Inc. including, for example in U.S. Pat. Nos. 6,450,807, and 5,975,893, as well as on the company's website, which is accessible on the World Wide Web (see, e.g., the url "www.invisalign.com"). The Invisalign® System includes designing and/or fabricating multiple, and sometimes all, of the aligners to be worn by the patient before the aligners are administered to the patient and used to reposition the teeth (e.g., at the outset of treatment). Often, designing and planning a customized treatment for a patient makes use of computer-based 3-dimensional planning/design tools, such as Treat™ from Align Technology, Inc. The design of the aligners can rely on computer modeling of a series of planned successive tooth arrangements, and the individual aligners are designed to be worn over the teeth and elastically reposition the teeth to each of the planned tooth arrangements.

Both traditional and recently developed alternative methods of orthodontic treatment require an amount of time, sometimes up to two to three years or more, to accomplish repositioning of a patient's teeth, during which the patient must continue to tolerate the existing appearance of their teeth. With traditional orthodontics, the patient's appearance includes the patient's teeth in unfinished positions, which may include extruded or extracted teeth or interproximal spaces and visible braces. Even when braces are avoided by using alternative treatment methods, the patient's teeth are visible in their natural color and unfinished positions until treatment has progressed or finished.

BRIEF SUMMARY OF THE INVENTION

The present invention provides a removable orthodontic tooth positioning appliance with improved or selected appearance and related methods and systems. In contrast to an appliance where a patient's teeth are visible in their unfinished positions, a positioning appliance in accordance with the present invention can include a depiction of a set of teeth (e.g., the patient's teeth) having a desired appearance and/or in a selected arrangement, such as their finished or desired positions. Thus, in one embodiment, the present invention presents a treatment option with improved appearance during orthodontic treatment, eliminating the wait during which the patient's teeth are being repositioned toward their planned positions before an improved appearance is presented.

Thus, in one aspect, the present invention includes a removable orthodontic tooth positioning appliance, and related systems and methods, with an improved or selected outer appearance to represent teeth in a desired arrangement.

For a fuller understanding of the nature and advantages of the present invention, reference should be made to the ensuing detailed description and accompanying drawings. Other aspects, objects and advantages of the invention will be apparent from the drawings and detailed description that follows.

BRIEF DESCRIPTION OF THE DRAWINGS

FIG. 1 is an diagram showing the anatomical relationship of the jaws of a patient.

FIG. 2A illustrates in more detail the patient's lower jaw and provides a general indication of how teeth may be moved by the methods and apparatus of the present invention.

FIG. 2B illustrates a single tooth from FIG. 2A and defines how tooth movement distances are determined.

DETAILED DESCRIPTION OF THE INVENTION

Figure 2C:
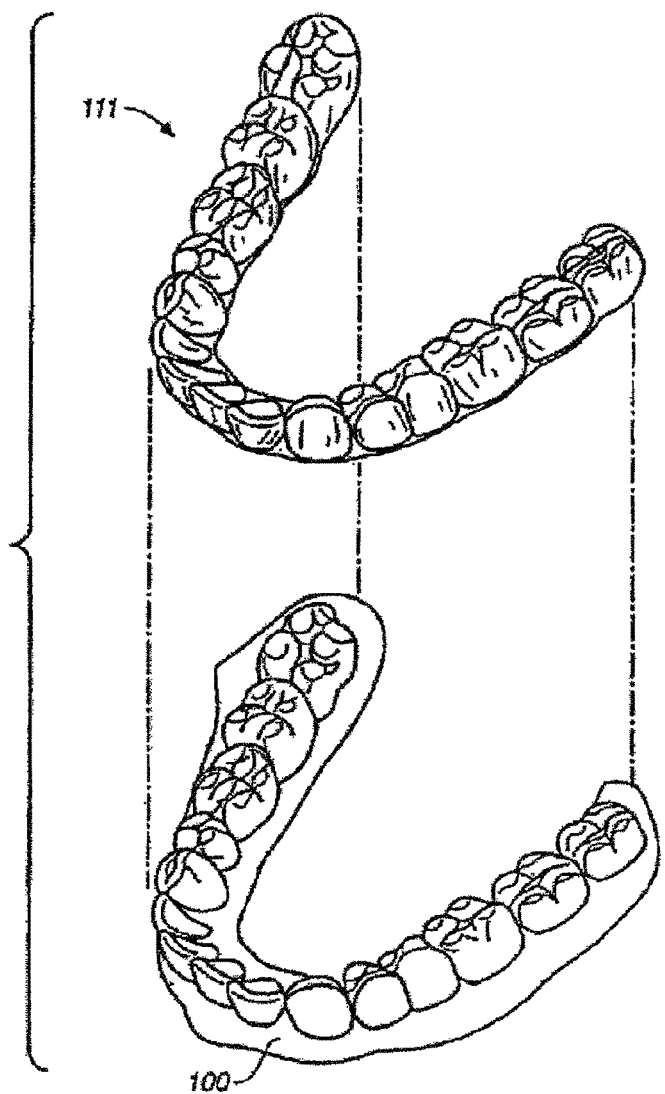
FIG. 2C illustrates the jaw of FIG. 2A together with an incremental position adjustment appliance without improved appearance.

The invention described herein provides a device, system, method and kit for a dental appliance with an outward appearance of a desired tooth arrangement that is different from the current teeth arrangement. As described in more detail below, the present invention can upon application instantly change or improve the appearance of a patient during orthodontic treatment through the use of a representation of teeth in a desired arrangement.

Functional Appliance without Improved Appearance Component

FIG. 1 provides an appropriate starting point in a discussion of the present invention with respect to appliances designed to apply positioning forces, or repositioning forces, to teeth. FIG. 1 depicts a skull 10 with an upper-jaw bone 22 and a lower-jaw bone 20. The lower-jaw bone 20 hinges relative to skull 10 at joint 30. Lower jaw bone 20 and upper jaw bone 22 further support lower jaw 100 and upper jaw 101 respectively.

Referring now to FIG. 2A, lower-jaw bone 100 includes a plurality of teeth 102, as is the case with most people. However, in many people, the arrangement of teeth 102 may include one or more teeth having positions and orientations that deviate from their optimum positions, thereby possibly forming an improper occlusion (malocclusion). Where significant deviations from optimal positions exist for one or more teeth 102, orthodontics treatment is often employed to move teeth towards their optimal positions. As a frame of reference describing how a tooth may be moved, an arbitrary centerline (CL) may be drawn through the tooth 102. With reference to this centerline (CL), each tooth may be moved in orthogonal directions represented by axes 104, 106, and 108 (where 104 is the centerline). The centerline of the tooth may be rotated about the axis 108 (angulation), axis 106 (inclination), and the axis 104 (rotation). Thus, all possible free-form motions of the tooth can be performed.

FIG. 2B shows how the magnitude of any tooth movement may be defined in terms of a maximum linear translation of any point P on a tooth 102. Each point P1 will undergo a cumulative translation as that tooth is moved in any of the orthogonal or rotational directions defined in FIG. 2A. That is, while the point will usually follow a nonlinear path, there is a linear distance between any point in the tooth when determined at any two times during the treatment. Thus, an arbitrary point P1 may in fact undergo a true side-to-side translation as indicated by arrow d1, while a second arbitration point P2 may travel along a curved path, resulting in a final translation d2. Many aspects of the present invention are defined in terms of the maximum permissible movement of a point P1 induced on any particular tooth. Such maximum tooth movement, in turn, is defined as the maximum linear translation of that point P1 on the tooth that undergoes the maximum movement for that tooth in any treatment step.

FIG. 2C shows one adjustment appliance 111 which is worn by the patient in order to achieve an incremental repositioning of individual teeth in the jaw 100. The appliance can include a shell (e.g., polymeric shell) having teeth-receiving cavities that receive and resiliently reposition the teeth. In one embodiment, a polymeric appliance can be formed from a known thin sheet of suitable elastomeric polymeric material, such a 0.03 inch thermal forming dental material by Tru-Tain Plastics, Rochester, Minn. An appliance can fit over all teeth present in an upper or lower jaw, or less than all of the teeth. In some cases, only certain teeth received by an appliance will be repositioned by the appliance while other teeth can provide a base or anchor region for holding the appliance in place as it applies force against the tooth or teeth targeted for repositioning. In some cases, many, most, or even all of the teeth will be repositioned at some point during treatment. Teeth which are moved can also serve as a base or anchor for holding the appliance as it is worn by the patient. Typically, no wires or other means are provided for holding an appliance in place over the teeth. In some cases, however, it may be desirable or necessary to provide individual anchors on teeth with corresponding receptacles or apertures in the appliance so that the appliance can apply a selected force on the tooth. Exemplary appliances, including those utilized in the Invisalign® System, are described in numerous patents and patent applications assigned to Align Technology, Inc. including, for example in U.S. Pat. Nos. 6,450,807, and 5,975,893, as well as on the company's website, which is accessible on the World Wide Web (see, e.g., the url "www.invisalign.com"). Appliances according to the present invention are further designed to include aspects such that the appliance is configured to operate in conjunction with one or more tooth movement devices disposed in the appliance itself and/or in an attachment mounted to a surface of a patient's tooth, as described herein.

An appliance can be designed and/or provided as part of a set or plurality of appliances. In such an embodiment, each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. A target tooth arrangement can be a planned final tooth arrangement selected for the patient's teeth at the end of all planned orthodontic treatment. Alternatively, a target arrangement can be one of many intermediate arrangements for the patient's teeth during the course of orthodontic treatment, which may include where surgery is recommended, where inter-proximal reduction (IPR) is appropriate, where a progress check is scheduled, where anchor placement is best, where palatal expansion is desirable, etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages. The adjustment appliances can be generated all at the same stage or in sets or batches (e.g., at the beginning of a stage of the treatment) and the patient wears each appliance until the pressure of each appliance on the teeth has fully been expressed or has resulted in the maximum allowable tooth movement for that given stage. A plurality of different appliances (e.g., set) can be designed and even fabricated prior to the patient wearing any appliance of the plurality. After wearing an appliance for an appropriate period of time, the patient replaces the current appliance with the next appliance in the series until no more appliances remain. The appliances are generally not affixed to the teeth and the patient may place and replace the appliances at any time during the procedure (e.g., patient-removable appliances).

Selected/Improved Appearances for the Functional Appliance

Figure 3A:
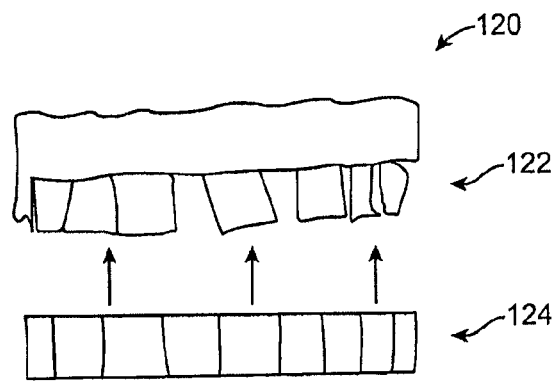
FIGS. 3A-3C illustrate the installation of an incremental position adjustment device with improved appearance in accordance with the present invention on a patient's upper teeth.

Referring now to FIG. 3A, a simplified illustration depicting a typical malocclusion 122 and the installation of a removable orthodontic positioning appliance 124 for the upper teeth 120 in conformance with the present invention is provided. A person of ordinary skill in the art would appreciate that although this figure only depicts a set of upper teeth, the invention would equally apply to a set of corresponding lower teeth as well. As discussed above, a patient will install/wear any particular appliance for a period of time during which the appliance applies forces to the patient's teeth urging them along their paths toward their planned final positions by some incremental amount. The present invention provides a means by which to mask the actual existing appearance of the patient's teeth in their present positions by incorporating into the appliance a representation of teeth in desired locations on visible portions of the shell appliance. During use, the patient places the appliance with its associated representation of teeth over their teeth, thereby covering the patient's currently misplaced teeth with an appliance that depicts teeth in a desired arrangement while simultaneously functioning to reposition the patient's teeth toward their own desired locations.

Figure 3B:
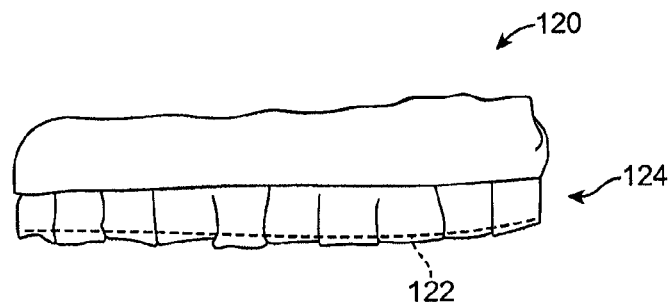
Figure 3C:
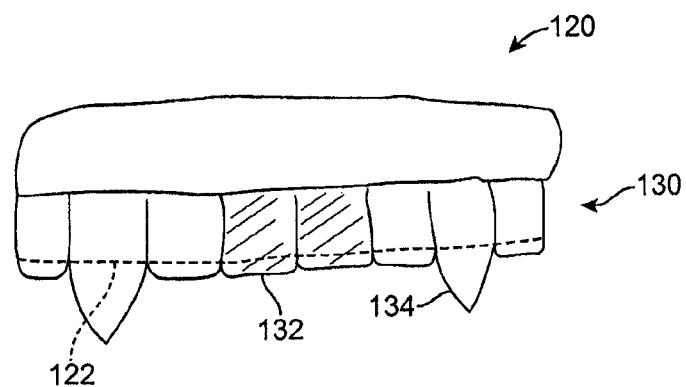

FIG. 3B, and FIG. 3C provide further illustration of the appearance enhancing qualities of the present invention. More specifically, FIG. 3B depicts the same individual from FIG. 3A, but is shown wearing the removable orthodontic positioning appliance 124 in conformance with the present invention. By comparing the appearance presented in FIG. 3B with the appearance presented in FIG. 3A, one can recognize that the teeth of FIG. 3B provide the appearance that the teeth are visually different from the actual arrangement of the patient's teeth at the given stage of treatment (e.g., desired orthodontic arrangement).

FIG. 3C further depicts how the appearance of the person of FIG. 3A can be altered by wearing a positioning appliance with a selected or improved appearance 130 in conformance with the present invention. The alternate embodiment shown incorporates a novelty arrangement in the form of a simulated gold tooth 132 and two fangs 134. Similar variations in appearance to that shown in FIG. 3C are possible, such as the incorporation of other novelty arrangements such as those selected for special occasions (e.g., exaggerated features like fangs, buck teeth, missing teeth, gapped teeth, crooked teeth, non-human teeth, gold or jeweled teeth, or chipped teeth). Another possible variation involves the use of red, white, and blue teeth segments, which might be used at least during the Fourth of July holiday or during other patriotic celebrations. Still another novelty arrangement would be to capture the appearance of an aesthetically desired arrangement, such as a model or celebrity tooth arrangement. With these examples, it should be appreciated that the concept of an improved or selected appearance can be subject to the particular desires of the patient without altering the desired orthodontic positioning and/or repositioning that the doctor may be trying to accomplish while the patient wears the appliances. Thus, the patient may request that the e by not modifying the basic appliance in areas where appearance is less important. An important consideration in selecting the arch span for the desired appearance is whether there will be a separate outer predetermined final tooth arrangement.

Integration of Functional Appliance with Selected/Improved Appearance Component

Figure 4A:
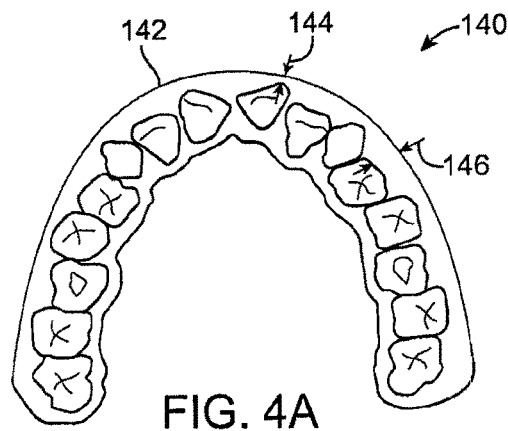
FIG. 4A illustrates a top down view of a person's lower teeth in an exemplary malocclusion while wearing an appliance in accordance with the present invention.
Figure 4B:
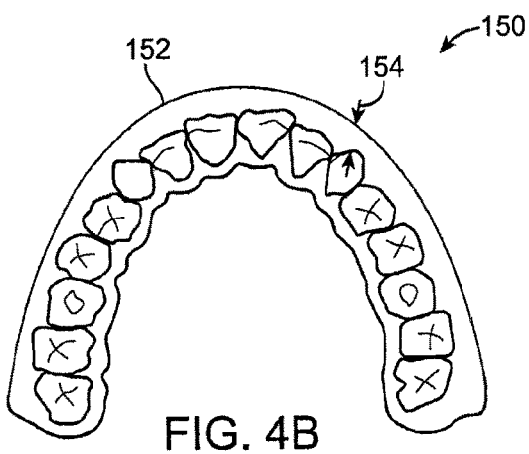
FIG. 4B illustrates a top down view of an inventive appliance being worn over the person's lower teeth after being moved by the appliance of FIG. 4A and shows how appliance thicknesses can be increased to maintain a desired outer surface appearance in accordance with one embodiment of the present invention.
Figure 4C:
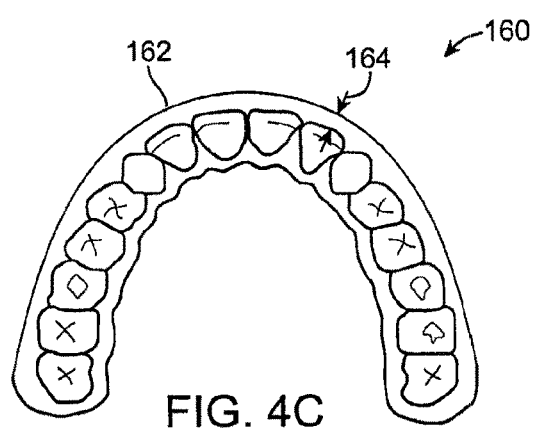
FIG. 4C illustrates a top down view of an inventive appliance being worn over the person's lower teeth after being moved by the appliance of FIG. 4B and shows how appliance thicknesses can be decreased to maintain a desired outer surface appearance in accordance with another embodiment of the present invention.

FIGS. 4A, 4B and 4C illustrate top down views of inventive appliances 140, 150, 160 being worn over a patient's teeth. FIG. 4A depicts appliance 140 being worn over the patient's teeth that have an exemplary initial malocclusion. Appliance 140 includes an outer surface 142 having a desired appearance. Outer surface 142 can be selected so as to envelope the patient's teeth. The outer surface selection can be made so as to result in a desired minimum thickness 144 and to minimize maximum thickness 146 to the extent possible given the malocclusion.

Depending on the malocclusion, the teeth may be tilted in to the mouth and rotated so that the desired final arch that is used to calculate the desired outer surface appearance at the prescribed teeth arrangement would never change, and thus the outer most position of the desired outer surface may not move outward during treatment. However, it is more likely that the outer surface of the appliance will extend further outward than the teeth will at any stage of treatment, wherein the outer surface of the appliance will only extend outward by the thickness of the material at the last stage.

FIG. 4B illustrates a top down view of the appliance 150 being worn over the person's lower teeth after being moved by the appliance 140 of FIG. 4A. FIG. 4B illustrates how appliance thicknesses (e.g., thickness 154) can be increased to maintain a desired outer surface appearance, such as when outer surface 152 is selected to be the same as outer surface 142 used for appliance 140 and the patient's teeth have been moved inwards.

FIG. 4C illustrates a top down view of the appliance 160 being worn over the person's lower teeth after being moved by the appliance 150 of FIG. 4B. FIG. 4C illustrates how the thicknesses of an appliance (e.g., thickness 164) can be decreased to maintain a desired outer surface appearance, such as when outer surface 162 is selected to be the same as outer surface 152 or 142 and the patient's teeth have been moved outwards.

Figure 5A:
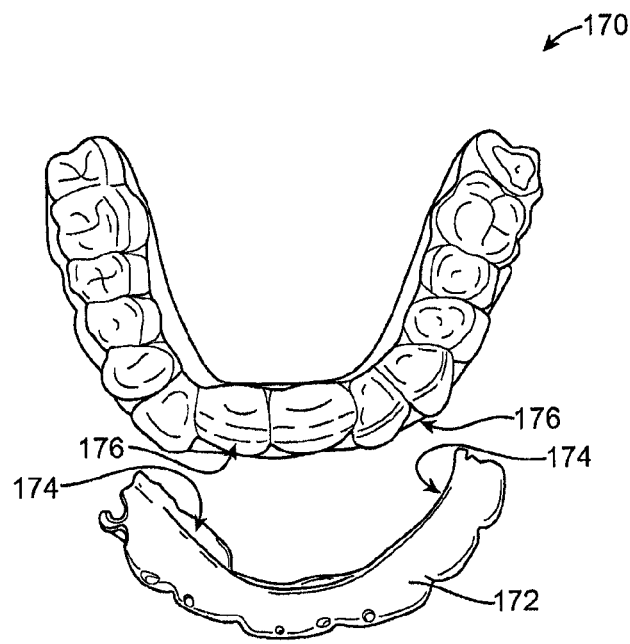
FIG. 5A illustrates separate components of one embodiment of the present invention, where the outer component is a veneer configured to be attached to the main body of the incremental position adjustment device.
Figure 5B:
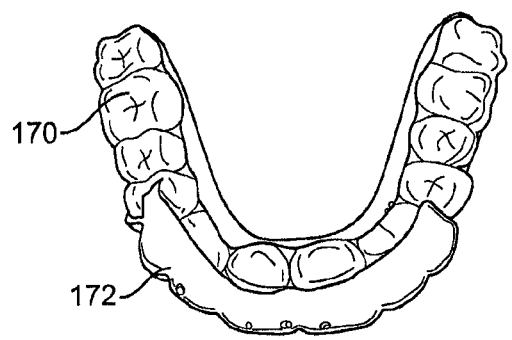
FIG. 5B illustrates the embodiment of FIG. 5A, where the outer component has been attached to the main body.

FIG. 5A and FIG. 5B illustrate one embodiment of a positioning appliance 170 for the lower teeth with improved appearance, where the desired appearance is provided by an attachable outer component 172. The attachable outer component shown is a veneer-type component 172. As used herein, a veneer-type component 172 (hereinafter "veneer") refers to a component that incorporates a desired appearance and may include attachment surfaces 174 that are substantially shaped to match mating exterior surfaces 176 of an appliance. The veneer shown incorporates outer surfaces that represents a patient's own teeth in their planned final arrangement. Alternatively, an outer component can be shaped to represent an ideal or selected set of teeth as described elsewhere herein. In FIG. 5A, the veneer outer component 172 is shown offset from the main body of the positioning appliance 170 so as to illustrate exemplary shapes for both a veneer-type outer component 172 and a main body of an appliance 170. FIG. 5B illustrates the combination of the veneer-type outer component 172 and the main body of the appliance 170.

As can be seen in FIG. 4A through FIG. 5B, the outer component can be configured to cover just a portion of the lingual surface and the anterior portion of the patient's arch or the full arch. Partial arch span coverage may be preferred since the posterior portions of the patient's arch are generally less visible, and such minimal coverage would require less material and thus weigh less in the mouth. To further decrease the amount of material used so as to decrease weight and/or increase comfort, the thickness of the component may be tapered as it extends toward the posterior portions of the mouth on the buccal side or as the component covers less visible surfaces of the teeth.

Various attachment features can be used to couple an outer component with an appliance main body. Such attachment features can be used with a variety of outer component types or configurations (i.e., not just a veneer-type outer component). For example, an adhesive compound suitable for use in a dental/oral environment can be used. An example of such adhesive is a light curable aligner adhesive such as ClearLoc® (Align Technology, Inc,) The adhesive can be permanent or temporary. Temporary adhesive would facilitate the re-usability of the outer component with multiple inner components. Alternatively, various physical attachment features (undercuts, rivets, snaps, etc) can be used to secure the outer component to the main body. Such attachment features can include one or more bumps, hooks, stepped ramps, or a combination thereof. For example, the outer component and the main body of the appliance can include one or more reciprocal attachment features, such as a male protrusion designed to snap fit within a corresponding female receptacle. Such snap fit attachment features can provide the ability to removably attach an outer component with an appliance main body. Another example would include where one or more physical attachment features are secured directly to one or more of the patient's teeth. Such direct attachment features are sometimes used to allow for the application of repositioning forces in certain directions. An outer component can be configured to attach to one or more of these direct attachment features. Alternatively, an outer component can be configured to engage with a protrusion or bump that may be formed in an aligner for another purpose, such as to engage a direct attachment feature secured to a tooth. As such, an outer component can be configured to couple with an appliance main body having a treatment specific design in a variety of ways. Alternatively, an outer component and the main body of the appliance can be integrally formed, thereby eliminating the need for attachment features.

In order to facilitate the use of a particular outer component with the main bodies of two or more distinct appliances, the attachment features on the outer component and the main bodies of the appliances can be designed accordingly. As will be appreciated by a person skilled in the art, many variations in attachment features are possible that provide the ability to couple an outer component to the main bodies of two or more different appliances. One such example would be the use of an indentation on the outer component that is wider or longer than an interfacing bump on the main body of a first appliance, thereby allowing the use of the indentation with a bump located in a slightly different location on the main body of a second appliance. Additional approaches are described below.

Digital Development and Fabrication

As will be discussed in more detail below, various aspects of treatment planning used for positioning appliances can be advantageously employed to provide removable positioning appliances with the appearance of a desired tooth arrangement. Such treatment planning can include, for example, planning methodologies and techniques as described in numerous patents and patent applications assigned to Align Technology, Inc. including, for example in U.S. Pat. Nos. 6,450,807, and 5,975,893, the entire contents of which are hereby incorporated by reference. During treatment planning, a digital representation of a patient's initial arrangement of teeth may be obtained by one of any number of methods, such as by scanning. The digital representation of the initial representation can be manipulated to produce a target arrangement or planned final arrangement digital representation. Both the initial arrangement digital representation and the planned final arrangement digital representation can be used to produce a series of intermediate arrangement digital representations. The intermediate arrangement represent planned intermediate positions for the patient's teeth as they are incrementally moved from their initial arrangement toward their planned final arrangements. The various arrangement digital representations produced can be used to define and/or produce a series of appliances for incrementally repositioning a patient's teeth from their initial arrangement toward their planned final arrangement. While treatment planning is described herein primarily in terms of computer based or digital techniques, it will be recognized that the present invention can include or make use of various non-digital based techniques, including use of physical dentition modeling.

A series of appliances for use during a stage or course of treatment can include repositioning appliances shaped or configured to incrementally reposition one or more teeth as the appliance is worn by the patient, and/or retention appliances shaped or configured to retain or hold teeth in a desired arrangement such as a current arrangement. As noted, a repositioning appliance can include a plurality of tooth receiving cavities with one or more of the cavities shaped to apply repositioning forces so as to incrementally move one or more of the patient's teeth to a new arrangement. A retention appliance may similarly include tooth-receiving cavities with at least some of the cavities shaped to apply retention or positioning force(s) so as to restrain the patient's teeth from moving from a desired or current arrangement. During a course of treatment, one or more appliances in the series of appliances of the treatment plan can be used to restrain the patient's teeth for various purposes, such as to restrain the patient's teeth during a period of time necessary to conduct an evaluation of whether the treatment is progressing as planned or after a prescribed position has been obtained so as to prevent a relapse.

Figure 6:
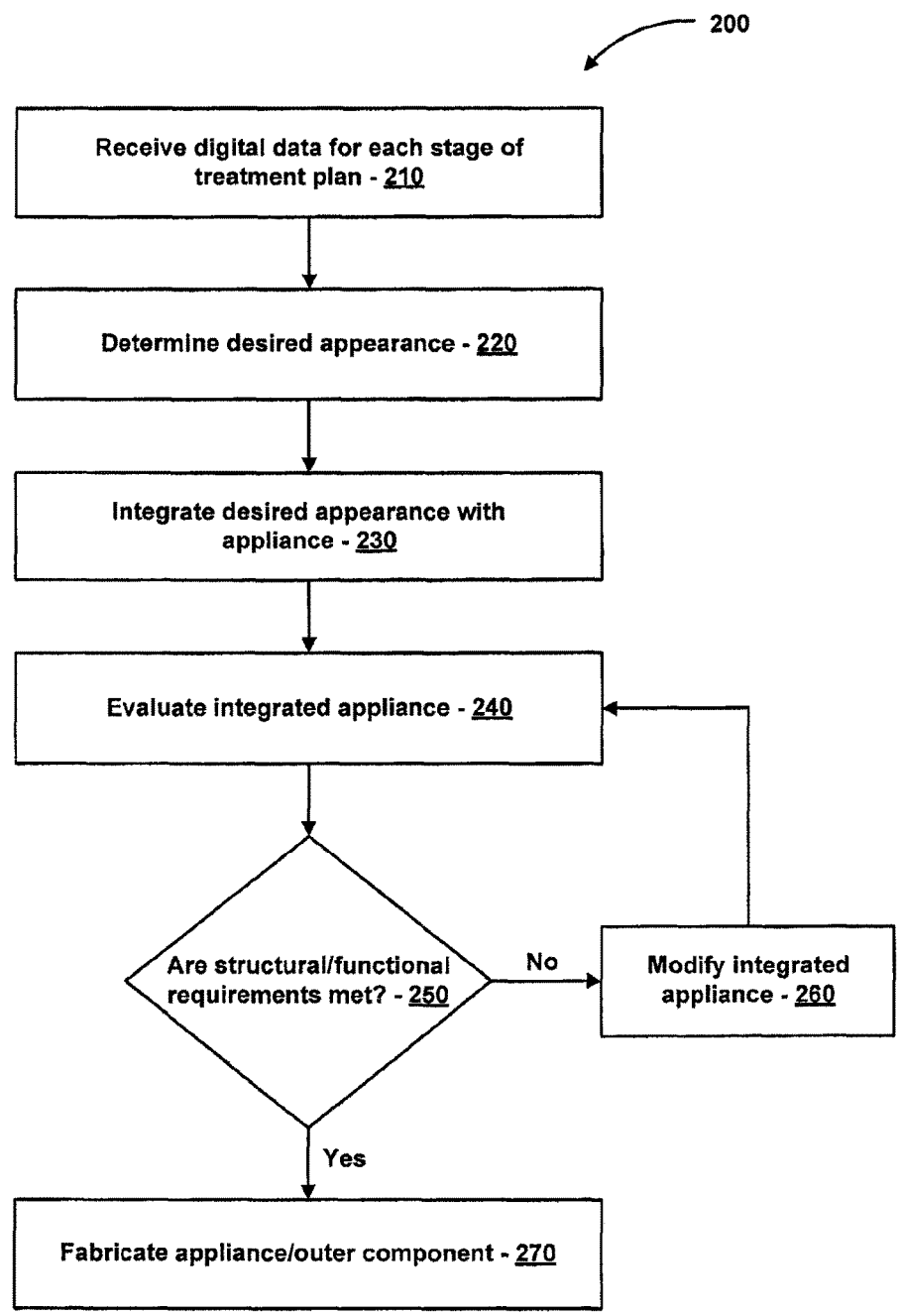
FIG. 6 is a block diagram illustrating steps for configuring and fabricating an incremental position adjustment device with improved appearance in accordance with an embodiment of the present invention.

Turning now to FIG. 6, an exemplary method 200 according to the present invention is illustrated. Individual aspects of method 200 are discussed in further detail below. While the following discussion is presented mainly in terms of digital development of an integrated appliance using computer aided design methods, it should be understood that non-digital methods can also be used and still be within the scope of the present invention.

As an initial step, data representing a patient's teeth at each stage of an orthodontic treatment plan is received or produced (step 210). Typically, data representing a patient's initial or current arrangement of teeth is manipulated to produce a planned final arrangement for the patient's teeth. Once the planned arrangement is produced, it is used in conjunction with the patient's initial or current arrangement to produce a number of intermediate tooth arrangements or stages, which are subsequently used to configure respective individual position adjusting appliances to sequentially move the patient's teeth between each of the stages. Although step 210 is illustrated as receiving digital data for each stage of the treatment plan, as discussed above, such data can alternatively be generated as discussed above.

In steps 220 and 230, the desired appearance is determined and integrated within a treatment plan by integrating the desired appearance with one or more tooth positioning appliances corresponding to the treatment plan. As was discussed above, and as will be discussed in further detail below (see, e.g., FIGS. 7 and 8), both of these steps can involve many possible actions and related options. Because these steps are discussed in further detail below, further discussion here is omitted.

In step 240, the integrated appliance having the desired appearance can be optionally evaluated to determine whether structural and/or functional requirements are met. Exemplary structural and functional requirements can include a wide range of possible requirements, such as: flexibility; desired color, look, and feel; retention characteristics; weight; thicknesses required for the material or fabrication process used; resulting teeth positioning force characteristics; and protective characteristics. Evaluation of appliance flexibility and teeth positioning force characteristics can be accomplished by a variety of methods, such as by finite element analysis or by a suitable parametric method. Exemplary finite element analysis methods that can be employed are described in U.S. Pat. No. 7,320,592, entitled "DEFINING TOOTH-MOVING APPLIANCES COMPUTATIONALLY," the entire content of which is hereby incorporated by reference. Evaluation of structural and/or functional requirements can be accomplished with the aid of a conventional physical force measurement system or by a virtual interaction with the integrated appliance, such as by display of the integrated appliance on a suitable display screen. Exemplary physical force measurement system and method that can be employed are described in U.S. patent application Ser. No. 11/881,528, entitled "ORTHODONTIC FORCE MEASUREMENT SYSTEM." Such virtual interaction can also include display of a virtual representation of the patient's teeth, either simultaneous with the display of the integrated appliance, or alone. Such virtual interaction can help with the assessment of a range of structural or functional requirements, such as desired color, look, feel, and retention characteristics. Computer implemented methods can also be used to determine the resulting weight of an integrated appliance.

An integrated appliance having the desired appearance can also include a protective arrangement, such as a mouth guard used during various sporting activities. The appliance material and thicknesses used can influence the level of protection that such a protective arrangement provides. Appliance material properties can be considered in determining the configuration of the appliance so as to obtain the desired level of protection. The desired level of protection may vary with the characteristics of the sport played, such as position played, age of the player, the aggression level of the player, and the like. The protective arrangement can be configured to reduce injury in a variety of ways, such as by providing a cushioning effect so as to reduce peak force levels transmitted within the body during an impact, and/or by providing for dispersion of localized impact forces to surrounding tissues. Dispersion of localized impact forces can be enhanced by configuring the appliance having a protective arrangement to interface with teeth from the patient's upper and lower arches of teeth, thereby providing for additional dispersion of impact forces.

In step 250, the results of any evaluation of the integrated appliance can be used to decide whether to modify the integrated appliance. In step 260, the integrated appliance can be modified as desired. A wide range of modifications are possible. For example, modifications can include any changes necessary to ensure that the integrated appliance meets any of the structural and/or functional requirements evaluated in step 240. Many modifications to the integrated appliance can be accomplished with the aid of automated methods. For example, an algorithm can be used to guide modification of the integrated appliance so as to achieve improved force and weight characteristics of the resulting appliance. Known computer aided design methods can be used to modify the integrated appliance. The modified integrated appliance can then be re-evaluated as described above in step 240. Evaluation and modification of the integrated appliance can be repeated as desired until a final integrated appliance configuration is achieved. Once the integrated appliance and/or outer component have been digitally defined, they can be fabricated (step 270).

Figure 7:
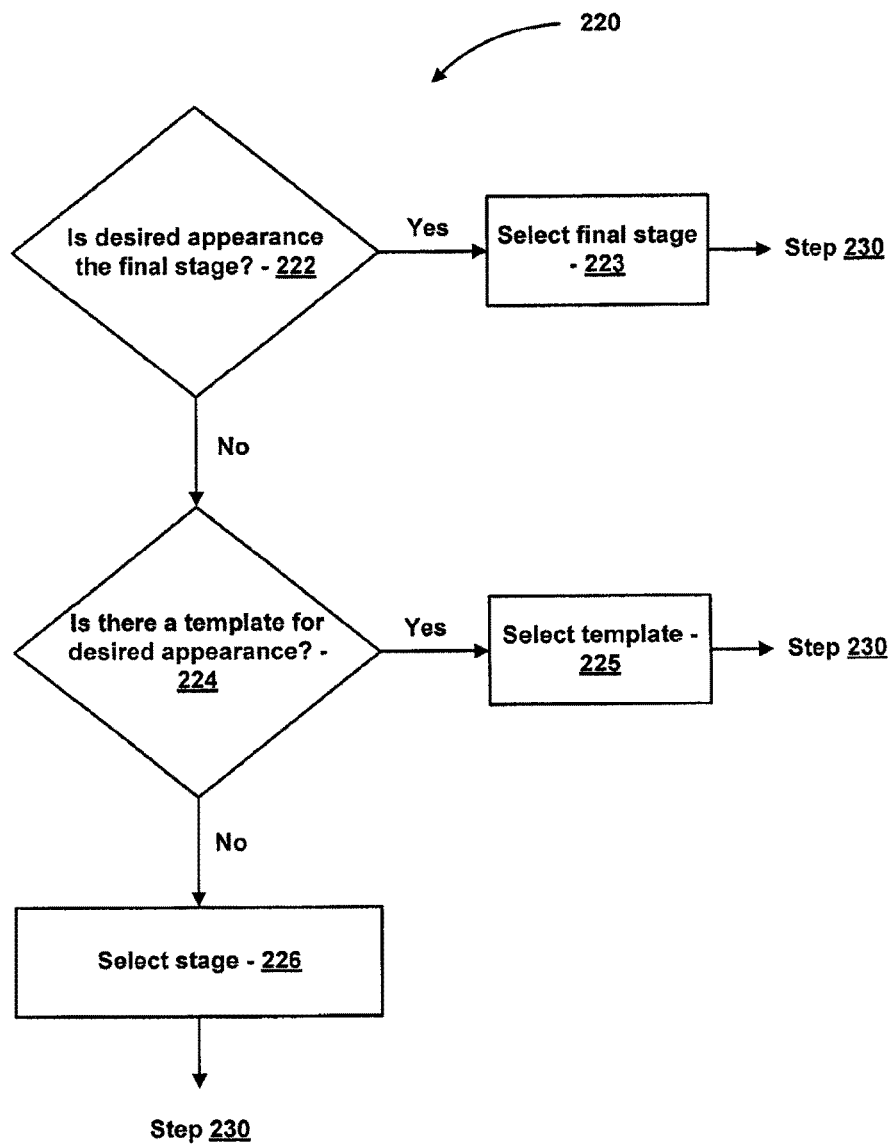
FIG. 7 is a block diagram illustrating steps for determining desired appearance in accordance with an embodiment of the present invention.

Turning now to FIG. 7, an exemplary method for determining the desired appearance (step 220) will now be described. Although a wide range of possible sources of desired appearances are possible, the method of FIG. 7 shows three such sources. In steps 222 and 223, the final orthodontic treatment stage tooth arrangement for the patient can be selected as the desired appearance. Selection of the patient's final treatment stage tooth arrangement may provide a number of benefits, such as providing the patient with their future appearance prior to the end of the course of orthodontic treatment. This can help to motivate the patient to continue with the planned orthodontic treatment or allow the patient to see and experience their desired appearance and make changes if unsatisfied.

In steps 224 and 225, the desired appearance can also be selected from a number of predetermined digital templates of a wide range of possible desired appearances. For example, such digital templates can include digital models of one or more ideal teeth, and can also include digital models of novelty tooth arrangements. These templates can include any number of individual teeth, from one to an entire arch. The desired appearance can also be selected to include a combination of one or more of the patient's teeth in a selected treatment stage arrangement and one or more teeth from one or more selected templates. For example, the desired arrangement can be a novelty arrangement, such as an arrangement for Halloween that includes two fanged teeth 134 in place of the canine teeth of the upper arch (see FIG. 3C). Such an arrangement can be formed by a mixture of the patient's teeth in a selected treatment stage (such as the final treatment stage) and two fanged teeth from one or more fang tooth templates. In another example, the desired arrangement can be a novelty arrangement for a holiday that includes one or more template teeth representations in place of one or more of the patient's teeth, such as the patient's maxillary central incisors. As discussed above in connection with FIG. 3C, many variations are possible and can be incorporated into template representations that can be used to formulate the desired appearance. As illustrated in step 226, treatment stages other than the final stage tooth arrangement for the patient can be used to formulate the desired appearance.

Figure 8:
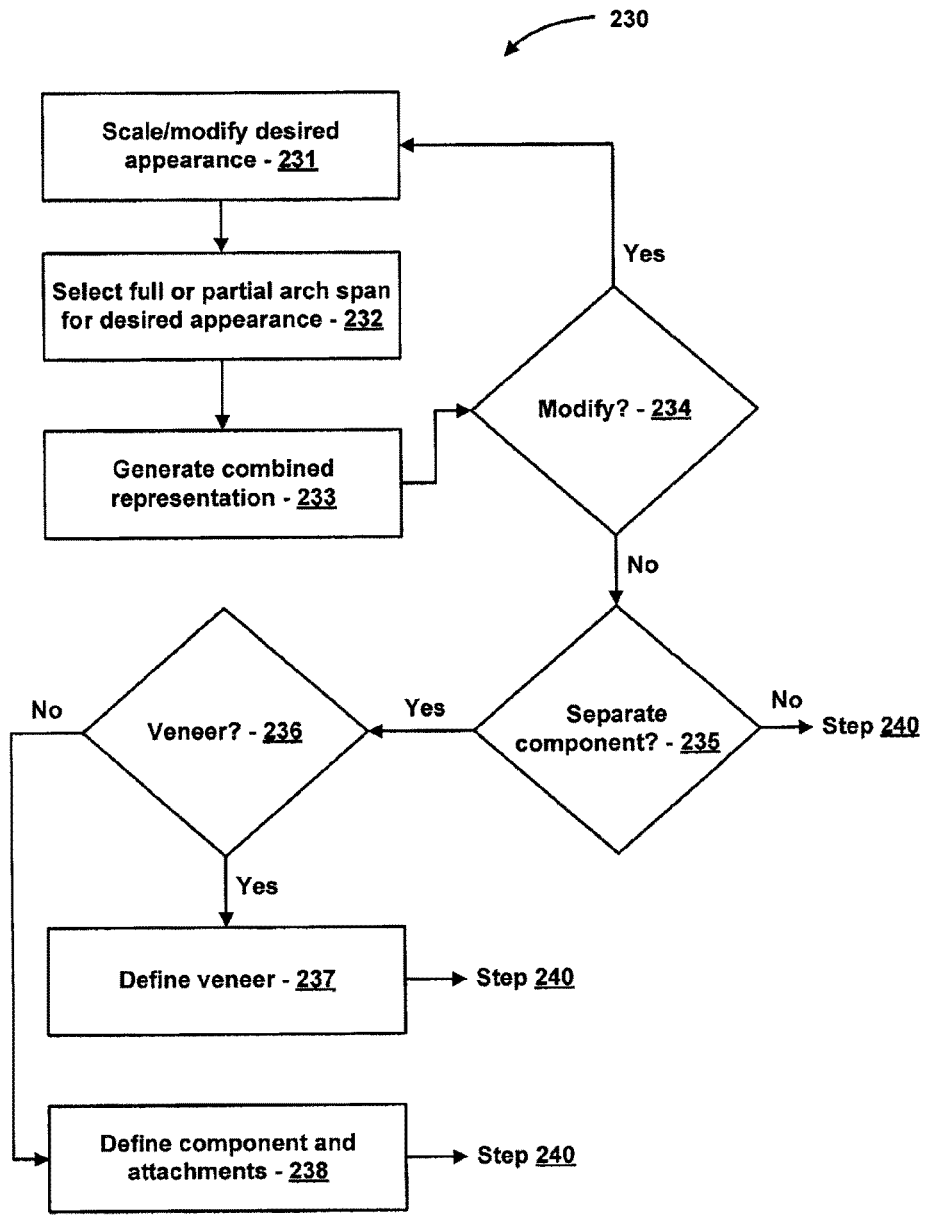
FIG. 8 is a block diagram illustrating steps for integrating desired appearance with an appliance in accordance with an embodiment of the present invention.

Turning now to FIG. 8, an exemplary method for integrating the desired appearance with an appliance (step 230) will now be described. In steps 231, 232, 233, and 234, the exterior configuration of the integrated appliance is configured. It should be appreciated that the order of the steps shown is not required, and that the steps can be practiced in any desired sequence. For example, it may be preferred to first generate a combined representation (step 233) prior to scaling/modifying the desired appearance (step 231). The generation of a combined representation (step 233) can involve the virtual combination of digital models for the basic positioning appliance with digital models for the selected desired appearance. Evaluation of this combined representation can help determine whether, or by how much, to scale and/or modify the digital models for the selected desired appearance. Scaling of the digital models for the selected desired appearance can be used to provide for desirable proportions in the resulting combined representation. Modification of the digital models for the selected desired appearance can include relative positional modifications to ensure proper placement/orientation of the selected desired appearance digital models.

In step 231, the digital models for the desired appearance can be scaled and/or modified. At least where the selected desired appearance is the patient's teeth in their final treatment stage, it will typically be advantageous to scale up the desired appearance so as to generate a combined representation (step 233) where the outward facing visible surfaces of the combined representation are defined by the scaled up desired appearance. Without such scaling and/or modification, the outward facing visible surfaces of the combined representation would typically be at least partially defined by outward facing visible surfaces of the basic positioning appliance at that stage of treatment.

By scaling and/or modifying the patient's final teeth positions so as to substantially or wholly envelope the outward facing visible surfaces of the basic positioning appliances, a combined representation can be generated that has outward facing visible surfaces that are substantially or wholly defined by the scaled and/or modified selected desired appearance.

In another embodiment, the desired appearance digital models can be scaled by a varying amount, such as scaling a particular portion of the desired appearance by some amount, such as 10%, and progressively reducing the scaling factor for the other portions of the desired appearance. For example, by scaling posterior portions of the desired appearance by greater amounts than anterior portions of the desired appearance, the scaled desired appearance can provide a wider appearance that may serve to accentuate a patient's smile. When the desired appearance has been selected to include one or more digital template models, it may be necessary to scale and/or modify the template derived virtual teeth representations so their sizes and positions provide the desired appearance in the integrated appliance.

Where the selected desired appearance is scaled and/or modified, various approaches can be used with regard to the amount of scaling and/or modification. In a first approach, the selected desired appearance can be scaled and/or modified so that it substantially or wholly envelopes the forward visible surfaces of a particular basic appliance in the overall series of appliances, for each appliance (see, e.g., FIG. 4C). This first approach may result in an integrated appliance with a minimum amount of material usage and least weight, but the outer surface may move inward and outward during treatment until it is finally positioned outward by the thickness of the appliance material during the last stage of treatment. However, this first approach may require more developmental expense due to the added scaling and/or modification effort necessary for each basic appliance in a series of appliances involved. In a second approach, the selected desired appearance can be scaled and/or modified so that it substantially or wholly envelopes the forward visible surfaces of a series of appliances (see, e.g., FIG. 4B). While this second approach may result in the use of additional amounts of material usage for some particular basic appliances in the series of appliances involved, it will maintain the outer surface position and appearance until the later stages and may reduce developmental expense due to the use of a common scaled and/or modified desired appearance as would be required with the first approach (see, e.g., FIG. 4C). Additional approaches can also be used, such as a mixture of the above discussed first and second approaches. For example, the second approach can be used earlier in the treatment where the patient's teeth are further away from their targeted final positions, and the first approach can be used later in the treatment as the patient's teeth approach their targeted final positions.

The amount of any scaling and/or modification can also be influenced by integration considerations. Where a separate veneer-type outer component will be integrated with an appliance main body, the resulting thickness of the veneer-type outer component may be an important consideration, and the selected desired appearance can be scaled and/or modified to ensure that the veneer-type outer component meets minimum thickness requirements. Where one or more attachment features are used to secure a separate outer component to an appliance main body, the amount of scaling and/or modification can be adjusted to ensure adequate space for these attachment features.

Modification can also be used to improve the appearance for the resulting integrated appliance (i.e., the basic appliance and the associated outer component). For example, it may be desirable to scale and/or modify the desired appearance digital models where there are regions where the basic position adjusting appliance protrudes beyond the outward facing visible surfaces of the combined representation. Modification can also be used to enhance the color of the appliance, such as in regions with relatively thin wall thickness between the outer surface and a particular tooth.

In step 232, the arch span for the desired appearance is selected. The selected span can include one or more partial arch spans, or can be the entire arch. For example, the selected span can be limited to the more visible anterior teeth. Limiting the selected span to the more visible portions of the arch can help to avoid adding weight, size, and expense to the integrated appliance by not modifying the basic appliance in areas where appearance is less important. An important consideration in selecting the arch span for the desired appearance is whether there will be a separate outer component for the desired appearance, or whether the desired appearance outer component will be integral with the basic positioning appliance (step 235). As shown in FIGS. 5A and 5B, limiting the selected arch span to the more visible anterior teeth can result in a smaller separate outer component that is more easily integrated with the basic positioning appliance. When the desired appearance outer component will be integral with the basic positioning appliance, the selected arch span may have less of an impact on how easily the outer component is integrated with the basic appliance.

When a separate outer component is selected (in step 235), the method of FIG. 8 includes additional steps for integrating the separate outer component with the basic positioning appliance. It should be appreciated that there are many possible approaches for integrating a separate outer component with a basic appliance. FIG. 8 includes two such approaches, specifically an outer component configured as a veneer-type component (step 237), and an outer component that is integrated with a basic appliance by way of adhesive or one or more discrete attachments (step 238).

A known adhesive can be used to fix the component to the basic appliance. The step of adhering the component can occur during manufacturing or after the appliance and component have been shipped to the doctor or user. By fixing the component to the appliance, the user would only have one product to worry about storing, wearing, cleaning or losing. However, just because the component may be adhered to one appliance, does not mean the next component cannot be attached to the appliance by one or more discrete attachments.

As shown in FIGS. 5A and 5B, one of the many possible approaches for integrating a separate outer component involves using a veneer-type outer component (step 237). Such a veneer-type outer component can be defined using a variety of different approaches. For example, the veneer-type outer component can be digitally defined by performing a volume or solid subtraction of the virtual representation of the basic positioning appliance from the combined virtual representation. The resulting virtual representation of the veneer-type outer component can be further modified by subtracting additional portions from interfacing surfaces of the veneer-type outer component so as to provide room for an adhesive layer between the veneer-type outer component and the basic positioning appliance. As a further example, the combined representation can be divided into two or more virtual parts by using a selected interface surface, where one of the resulting virtual parts corresponds to the main body of the basic positioning appliance and the other resulting virtual part(s) corresponds to the veneer(s). The interface surface can be selected so as to provide interfacing surfaces of the basic appliance and the veneer with preferred characteristics, such as superior retention, or the ability to use a particular outer component with two or more different basic positioning appliance main bodies for two or more stages of an orthodontic treatment plan. When the same outer component veneer is to be used with two or more different basic appliance main bodies, the appliance main bodies can be configured with a common interface surface configuration corresponding to a matching surface on the common veneer-type outer component.

A separate outer component can also be integrated with a basic appliance main body using one or more discrete attachments (step 238). Although a single discrete attachment is possible where the attachment has sufficient rigidity, typically two or more discrete attachments would be used. It should be appreciated that a variety of different discrete attachments can be used. For example, the separate outer component and one or more basic appliance main bodies can be designed with complementary snap-fit features, such as a protrusion shaped to be received and retained within a complementary shaped receptacle. As additional examples, a discrete attachment can include one or more bumps, hooks, stepped ramps, or a combination thereof. The one or more discrete attachments can also be designed so as to allow the use of a particular separate outer component with two or more different basic appliance main bodies. For example, the discrete attachment(s) on one basic appliance main body can share the same relative spatial orientation with the discrete attachment(s) on a different basic appliance main body, thereby providing identical interface points for use with a common separate outer component. As an additional example, the discrete attachment(s) on different basic appliance main bodies can be designed with limited directional clearances sufficient to account for different relative spatial orientations of the attachment(s) so as to couple with a common separate outer component. By using any of the above attachment configurations, the user can remove the outer component at any time. Reasons for removing the outer component may include cleaning, changing to present the patient's own appearance, changing to a new appearance, or just to remove the extra weight, discomfort, or awareness of the presence of the extra component.

It should be understood that a wide range of shapes and sizes of components are possible. In one embodiment, an outer component can include a substantially uniform or similar thickness (e.g., buccal to lingual thickness) partially or wholly along the arch span of the component. In another embodiment, the component can include a varied or substantially non-uniform thickness (e.g., buccal to lingual thickness) along at least a portion of the arch span of the component. For example, component thickness can gradually increase or decrease along an incisor-to-molar or crown to gingival direction along a span of the arch. In yet another embodiment, the component can include substantially changing thickness (e.g., buccal to lingual thickness) between adjacent teeth so as to account for variations in distances between the outer surfaces of adjacent teeth and corresponding portions of the desired appearance as might arise when one or more of a patient's teeth are significantly displaced from their planned final position (see, e.g., FIGS. 4A-4C). Thus, the lingual side and occlusal surface of the aligner will typically be thick enough to provide the desired force to move or retain the teeth. In addition, those aspects of the aligner on the buccal side that are not visible when the user opens their mouth or smiles may be thick enough to provide the desired force to move or retain the teeth.

Figure 9:
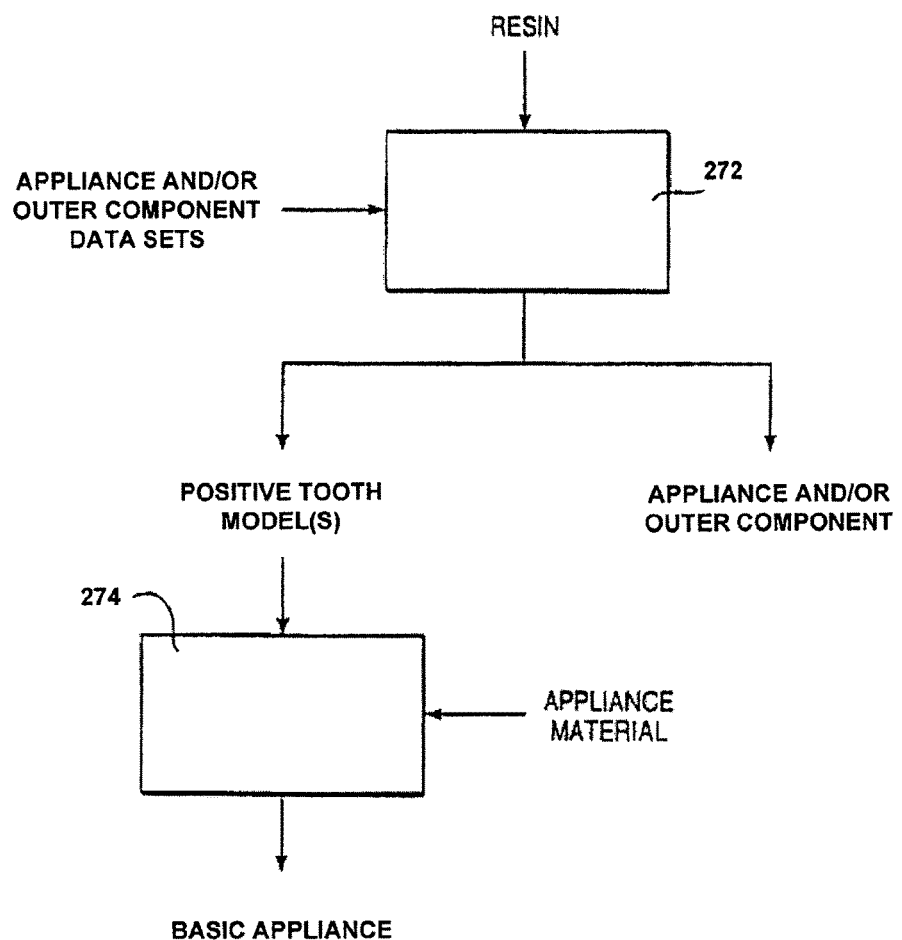
FIG. 9 illustrates alternative processes for producing an appliance and/or outer component with the appearance of a desired tooth arrangement according to methods of the present invention utilizing digital data sets representing the appliance and/or outer component.

Once an appliance (e.g., integrated appliance) and/or outer component have been digitally defined, they can be fabricated as illustrated in FIG. 9. Fabrication methods can employ a rapid prototyping device 272 such as a stereo lithography or digital light projector machine. An exemplary rapid prototyping machine is available from 3D System, Valencia, Calif. or EnvisionTEC, Gladbeck, Germany. The rapid prototyping machine 272 will selectively harden a liquid or other non-hardened resin into a three-dimensional structure which can be separated from the remaining non-hardened resin, washed, and used either directly as the appliance and/or outer component, or indirectly as a mold for producing the appliance. The prototyping machine 272 will receive the individual digital data sets corresponding to the integrated appliance and/or outer component, and produce one structure corresponding to each.

In some cases, the rapid prototyping machine 272 can be used to produce molds which are, in effect, positive tooth models of each successive stage of the treatment. After the positive models are prepared, a conventional thermal vacuum forming machine 274 can be used to produce the basic appliances from a more suitable material, such as 0.03 inch thermal forming dental material. The machine 274 produces each of the basic appliances directly from the positive tooth model and the desired material.

Where the outer component is produced as a separate veneer-type component, it can be produced by a variety of different fabrication techniques, including stereolithography (using ABS material, for example), an automated computer aided cutting (e.g., CNC machine) or molding process or even manually by providing a plastic template to the attending dentist for use in the creation of a separate veneer-type outer component (using acrylic plastic, for example). A veneer-type outer component can be fabricated using a variety of readily available dental materials such as plastics, ceramics, and composite materials in a variety of color shades. Ideally, these conventional materials would be extruded into a hollow shell to form the required veneer-type component and then self-cure at room temperature or under the activation assistance of UV light into a hard rigid stain-resistant structure.

Figure 10:
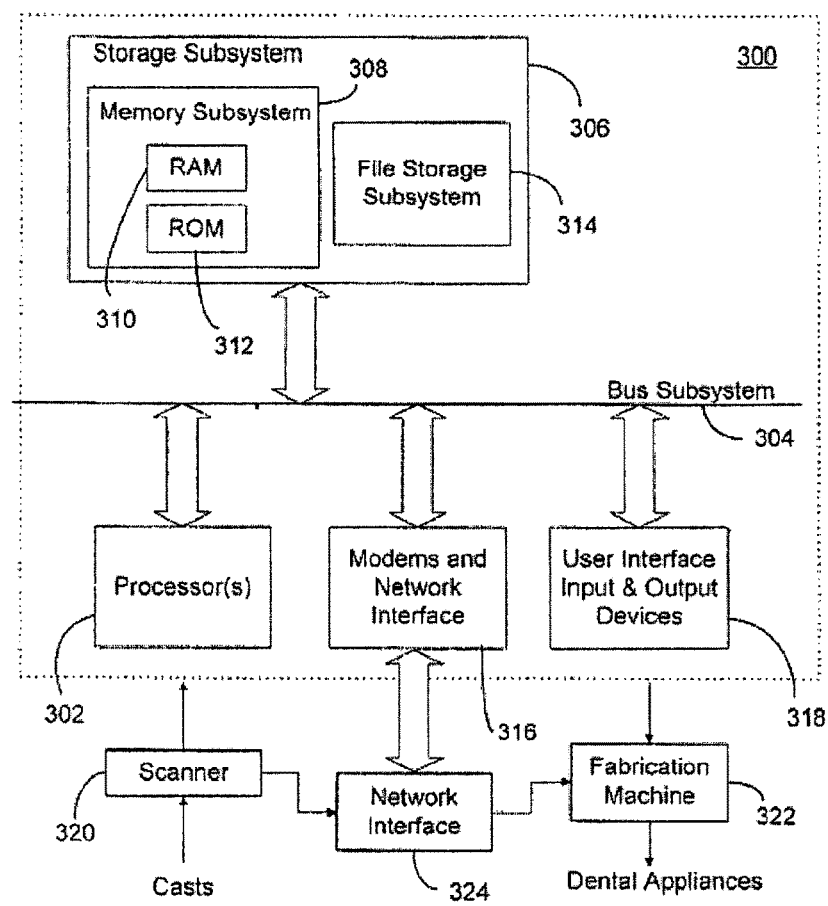
FIG. 10 is a simplified block diagram of a data processing system incorporating an embodiment of the present invention.

FIG. 10 is a simplified block diagram of a data processing system 300 embodying the present invention. Data processing system 300 typically includes at least one processor 302 which communicates with a number of peripheral devices via bus subsystem 304. These peripheral devices typically include a storage subsystem 306 (memory subsystem 308 and file storage subsystem 314), a set of user interface input and output devices 318, and an interface to outside networks 316, including the public switched telephone network. This interface is shown schematically as "Modems and Network Interface" block 316, and is coupled to corresponding interface devices in other data processing systems via communication network interface 324. Data processing system 300 can be a terminal or a low-end personal computer or a high-end personal computer, workstation or mainframe.

The user interface input devices typically include a keyboard and may further include a pointing device and a scanner. The pointing device may be an indirect pointing device such as a mouse, trackball, touchpad, or graphics tablet, or a direct pointing device such as a touch screen incorporated into the display. Other types of user interface input devices, such as voice recognition systems, are also possible.

User interface output devices typically include a printer and a display subsystem, which includes a display controller and a display device coupled to the controller. The display device may be a cathode ray tube (CRT), a flat-panel device such as a liquid crystal display (LCD), or a projection device. The display subsystem may also provide non-visual display such as audio output.

Storage subsystem 306 maintains the basic programming and data constructs that provide the functionality of the present invention. The software modules discussed above are typically stored in storage subsystem 306. Storage subsystem 306 typically comprises memory subsystem 308 and file storage subsystem 314.

Memory subsystem 308 typically includes a number of memories including a main random access memory (RAM) 310 for storage of instructions and data during program execution and a read only memory (ROM) 312 in which fixed instructions are stored. In the case of Macintosh-compatible personal computers the ROM would include portions of the operating system; in the case of IBM-compatible personal computers, this would include the BIOS (basic input/output system).

File storage subsystem 314 provides persistent (non-volatile) storage for program and data files, and typically includes at least one hard disk drive and at least one disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected via various local-area or wide-area network media, including telephone lines. Similarly, the input devices and display need not be at the same location as the processor, although it is anticipated that the present invention will most often be implemented in the context of PCs and workstations.

Bus subsystem 304 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 320 is responsible for scanning casts of the patient's teeth obtained either from the patient or from an orthodontist and providing the scanned digital data set information to data processing system 300 for further processing. In a distributed environment, scanner 320 may be located at a remote location and communicate scanned digital data set information to data processing system 300 via network interface 324.

Fabrication machine 322 fabricates dental appliances based on data set information received from data processing system 300. In a distributed environment, fabrication machine 322 may be located at a remote location and receive data set information from data processing system 300 via network interface 324.

It is understood that the examples and embodiments described herein are for illustrative purposes and that various modifications or changes in light thereof will be suggested to persons skilled in the art and are to be included within the spirit and purview of this application and the scope of the appended claims. Numerous different combinations are possible, and such combinations are considered to be part of the present invention.

What is claimed is:

1. A method for fabricating at least one modified teeth moving appliance, the method comprising:

receiving a digital representation of a patient's teeth for a plurality of stages of treatment of a treatment plan from an initial arrangement of the patient's teeth to a target arrangement of the patient's teeth;

receiving a digital representation of teeth in a selected arrangement, the selected arrangement being different than an actual arrangement of the patient's teeth, wherein the selected arrangement represents one or more of the target arrangement and a desired outcome of the treatment plan;

creating an appliance main body digital representation of a plurality of appliance main bodies, each of the plurality of appliance main bodies for moving the patient's teeth between two stages of the plurality of stages of treatment, each appliance main body having teeth receiving cavity geometries shaped to receive and resiliently reposition the patient's teeth between the two stages of treatment;

modifying the appliance main body digital representation to create a digital representation of a modified teeth moving appliance comprising an inner component configured to receive the patient's teeth and apply a tooth-moving force to move the patient's teeth when worn and an outer component having an outer surface and is configured to couple with the inner component, the outer surface having an outer surface geometry shaped to depict the teeth in the selected arrangement and to mask the actual arrangement of the patient's teeth when worn while producing the same movement of the patient's teeth by the appliance as would be produced by the inner appliance alone; and fabricating, using the modified appliance main body digital representation, at least one modified teeth moving appliance for moving the patient's teeth in accordance with the treatment plan.

2. The method of claim 1, wherein the modifying step comprises scaling up the digital representation of teeth in the selected arrangement and integrating the scaled up representation with the appliance main body digital representation.

3. The method of claim 2, wherein the integrating step further comprises creating a digital representation of the outer component having the outer surface that provides the digital representation of teeth in the selected arrangement.

4. The method of claim 3, wherein the integrating step further comprises creating one or more digital representations of complementary shaped attachment features for coupling the outer component with the at least the inner component.

5. The method of claim 1, wherein the teeth moving appliance further comprises a protective arrangement, a prescribed arrangement, or a novelty arrangement.

6. The method of claim 1, further comprising, further modifying the appliance digital representation based upon an algorithm, the algorithm addressing repositioning forces, weight, material thickness, or color of the outer surface.

7. The method of claim 1, further comprising, fabricating the modified teeth moving appliance and each other teeth moving appliance of the plurality of appliance main bodies before the onset of treatment of the patient.

8. The method of claim 1, wherein the actual arrangement comprises one or more of: an initial arrangement of the patient's teeth before application of the treatment plan and an intermediate arrangement of the patient's teeth.

9. The method of claim 1, wherein fabricating the at least one modified teeth moving appliance comprises thermally forming the at least one modified teeth moving appliance.

10. The method of claim 1, wherein the actual arrangement of the patient's teeth corresponds to a malocclusion condition affecting the patient's teeth.

11. The method of claim 10, wherein the outer surface has an outer surface thickness corresponding to the malocclusion condition.

12. The method of claim 1, wherein the outer component is configured to cover at least a portion of the lingual surface of the patient's teeth and at least a portion of an arch of the patient.

* * * * *